United States Patent [19]
Tubo et al.

[11] Patent Number: 5,145,770
[45] Date of Patent: Sep. 8, 1992

[54] CRYOPRESERVATION OF CULTURED EPITHELIAL SHEETS

[75] Inventors: Ross A. Tubo, Quincy; Susan F. Schaeffer, Wayland; Alexander Schermer, Belmont; Richard Odessey, Newton Lower Falls, all of Mass.

[73] Assignee: BioSurface Technology, Inc., Cambridge, Mass.

[21] Appl. No.: 533,385

[22] Filed: Jun. 4, 1990

[51] Int. Cl.$^5$ .................. C12N 5/00; A61K 35/36; A01N 1/02
[52] U.S. Cl. .................... 435/1; 435/240.1; 424/574; 62/62
[58] Field of Search ............. 435/240.2, 240.1, 1; 62/62, 64

[56] References Cited

U.S. PATENT DOCUMENTS

| | | | |
|---|---|---|---|
| 3,303,662 | 2/1967 | Moline | 62/62 |
| 4,695,536 | 9/1987 | Lindstrom et al. | 435/1 |
| 5,071,741 | 12/1991 | Brockbank | 435/1 |

FOREIGN PATENT DOCUMENTS 0296475 12/1988 European Pat. Off.
88/10068 12/1988 World Int. Prop. O.

OTHER PUBLICATIONS

Coriell Section I.A. [3] Preservation, Storage and Shipment; in Methods in Enzymology vol. LVIII, pp. 29–31; Jakoby & Pastan, Eds. Academic Press; New York, San Francisco, London 1979.
Hefton, et al. Cryopreservation of Cultured Epidermal Grafts A.B.A. (Abstract) Mar., 1988.
Neronov, et al. Cryopreservation of Rabbit Corneas by Combination of Dextran-40, Human Albumin and DMSO . . . Cryo Letters 10(5) 289–298 1989.
Eldad et al., 13(3) Burns 173 (1987), Cultured Epithelium as a Skin Substitute.
Heimbach et al., 208(3) Ann. Surg. 313–320 (1988), Artificial Dermis for Major Burns: A Multi-center . . .
McGann et al., 23(6) Cryobiology 574–575 (1986), Comparison of Dimethyl Sulfoxide and Dimethyl Sulfone . . . .
Cuono et al., 80(4) Plastic and Reconstructive Surgery 626 (1987), Composite Autologous-Allogeneic Skin . . .
De Luca et al., Symposium Cultured Epithelium (28 Mar. 1987), Human Epidermis Culture for the Treatment . . . .
Chang et al., 23(6) Cryobiology 573–574 (1986), The Effects of Cryoprotective Agent on . . . .
Korber et al., 23(6) Cryobiology 576 (1986), Cryopreservation of Human Platelet . . . .
May, 23(6) Cryobiology 569–570 (1986), Hypothermic Preservation of Skin: A Review of Current . . . .
Praus et al., 17 Cryobiology 130 (1980), Skin Cryopreservation.
May et al., 73 J. MAG. 233 (1984), Recent Developments in Skin Banking and the Clinical Uses . . . .
Baxter et al., XVII(6) (Suppl. 4) Transplantation Proceedings 112 (1985), Cryopreservation of Skin: A Review.
Taylor, (3(2) Cryobiology 192 (1966), Cryopreservation of Skin: Discussion and Comments.
Bondoc et al., 174(3) Ann. Surg. 371 (1971), Clinical Experience with Viable Frozen Skin . . . .

*Primary Examiner*—John Doll
*Assistant Examiner*—George C. Elliott
*Attorney, Agent, or Firm*—Testa, Hurwitz & Thibeault

[57] ABSTRACT

Disclosed is a method of cryopreserving a sheet of living, cultured epithelial cells for use as a skin wound dressing. The method ensures that the integrity of the sheet will be maintained, and it preserves a significant number of cells in a mitotically competent, physiologically healthy form. It involves use of a non cell penetrating cryoprotectant and certain freezing and thawing conditions.

28 Claims, 6 Drawing Sheets

CRYOPRESERVATION OF CULTURED EPITHELIAL SHEETS

BACKGROUND OF THE INVENTION

This invention relates to cryopreservation and long-term storage of cultured epithelial tissue sheets useful as skin wound dressings in a manner which maintains cell viability and colony-forming efficiency.

It has been a priority in the medical community to develop a skin wound dressing which will encourage new cell growth while preventing fluid loss and infection following skin wounds from burns, ulceration, or surgical excision. Since traditional dressings fail to protect large-scale wounds adequately, several alternatives have been developed. Among these alternatives are split- and full-thickness grafts of cadaver skin, porcine skin, and human allografts and autografts. Most have proved unsatisfactory since all but autografts eventually are rejected by the body in the absence of immunosuppressive therapy. In addition, use of conventional autografting techniques is not practical for massive burn injury involving large body surface areas.

Green et al. have developed a method of culturing epithelial cell sheets several cells thick for repairing burns, ulcerations and other skin wounds. U.S. Pat. No. 4,016,036 discloses the method for serially culturing keratinocytes to produce stratified sheets of epithelium. U.S. Pat. No. 4,304,866 discloses the method of producing transplantable cell sheets by culturing keratinocytes and detaching the sheet from its anchorage substrate using an enzyme such as dispase. U.S. Pat. No. 4,456,687 discloses agents useful to promote growth of epithelial cells. The disclosures of these patents are incorporated herein by reference. In the culture system developed by Green et al., epithelial cells divide rapidly on the surface of tissue culture dishes or flasks, and ultimately form a confluent, modestly stratified sheet of tightly interconnected cells. These confluent cultures can be released as a cohesive cell sheets by treatment, for example, with the enzyme dispase (see U.S. Pat. No. 4,304,866). The cultured sheets can then be attached to petrolatum impregnated gauze or other non adherent backing, transported in culture medium to the operating room, and applied to the patient.

Large burn surface areas can be covered with autograft materials prepared by these methods, but the autografts require time to culture. While the cells for autografting are being cultured, it is possible to maintain the wound with allograft material which is effective as a temporary wound dressing. Allograft material also promotes healing of chronic skin ulcers and split-thickness graft donor sites. Cultured autograft material prepared by the method of Green, et al. are now available commercially from Biosurface Technology, Inc., of Cambridge, Mass. Allograft material is available for experimentation and clinical testing.

A severe, very practical limitation on the use of cultured epithelial grafts is their inherent limited shelf-life. The viability and colony-forming efficiency of the sheets falls rapidly after they are removed from the substrate on which they grow. This restricts the time and distance the sheets may be shipped from production facility to the operating room. The cell sheets are extraordinarily fragile. They are normally able to maintain their ability to resume growth and to form colonies when applied to wounds only for about six to eight hours or less after dispase release. These temporal limitations preclude maintenance of a large inventory. Development of a cryopreservation method for extending the storage interval of the cultured sheets would permit maintenance of large inventories for shipment throughout the world.

The art is replete with descriptions of various tissue preservation methods including cryopreservation, use of special cell media, and certain packaging techniques. Cryopreservation allows for long-term storage by freezing the material in the presence of a cryoprotective agent. This agent displaces the aqueous material in and around the cells and thereby prevents ice crystals from forming. Numerous disclosed protocols vary the nature or amount of cryoprotective agent, and/or the time, course, or the temperature of the freezing process in an attempt to retain cell viability after a freeze/thaw cycle. See, for example, U.S. Pat. No. 4,559,298, U.S. Pat. No. 4,688,387.

Storing tissue by means of cryopreservation is a complicated and expensive process, capable of yielding highly variable results. However, no other approach has been shown to extend storage viability of animal tissue beyond very short periods, i.e., eight hours. See, for example, Pittelkow et al., 86 *J. Invest. Dermatol.* 4: 410–17, 413–14 (1986). For years skin banks have used frozen, human skin on burns as temporary allograft coverage. However, this frozen skin is not truly viable. Although banked skin is metabolically active, it is uncertain whether the epidermal cells can reproduce themselves. Heimbach, D., et al., "Artificial Dermis for Major Burns: a Multi-Center Randomized Clinical Trial", *Ann. Surg.* 313-320 (September 1988).

Large scale production of cultured epithelial autografts, as described by Green et al, promotes permanent coverage of large surface area wounds with the patients own skin. Although large amounts of cultured epithelium can be produced for patients, the limited shelf-life of the epithelium is a major concern. To this end, Cancedda and DeLuca have developed a protocol whereby confluent sheets of cultured keratinocytes are frozen in culture medium containing 10% glycerol (see EP 0 296 475). However, experience with this procedure indicates that cell recovery is variable and generally very low. In addition, the narrow time ranges of incubation makes this method impractical in large scale production. Moreover, grafts frozen with any protocol and then thawed after storage in liquid nitrogen often crack. Although wound coverage may be possible, the actual condition of the confluent sheets at the cellular level remains in question.

Early work using high molecular weight cryoprotectants showed that polyvinylpyrrolidone (PVP) or dextrans (MW 30–100Kd) alone prevents destruction of erythrocytes during cryopreservation Pegg, D. E., "Banking of Cells, Tissues and Organs at Low Temperatures", in *Current Trends in Cryobiology* (A. Smith, ed. 1970). Dextran and hydroxyethyl starch combined with glycerol will partly maintain the motility of frozen and thawed ram spermatazoa Schmehl et al., "The Effects of Nonpenetrating Cryoprotectants Added to Test-Yolk-Glycerol Extender on the Post-Thaw Motility of Ram Spermatazoa" 23 *Cryobiol.* 6:512-17 (1986).

Using trypan blue dye exclusion as a measure of viability, hydroxyethyl starch (HES) alone has been demonstrated to improve the survival of cryopreserved cells of hematopoietic origin, but only if the cryoprotectant was added and later removed in a slow, time-consuming manner (Conscience and Fischer, "An Improved Preservation Technique for Cells of Hemapoetic Origin" 22 *Cryobiol.* 5:495-98 (1985). This parameter of viability provides information only about short-term membrane stability and offers no data about the proliferative potential or long-term survival of the tissue. These authors concluded that HES did not offer any advantage for cryopreservation of cells of epithelial origin. In another study, HES was successfully used in the cryopreservation of cells of hematopoietic origin as determined by cell proliferation assays, a parameter that is more reflective of long-term viability (Wang, et al, *Cryobiol.* 24:229-237 (1987).

Studies using high molecular weight, non-penetrating (glass-forming) agents as cryoprotectants tend to focus on cells in suspension such as red blood cells and lymphocytes as described above. However, the need to maintain the integrity of a cohesive sheet of cells during cryopreservation places severe limitations on the recovery of viable cells (i.e., those with the capability of tissue regeneration).

It is an object of this invention to provide a cryopreservation methodology, capable of preserving a living, cultured sheet of epithelial cells, where the method maintains the structural integrity of the sheet, and preserves the mitotic competence of cells in the sheet, to permit formation of an epithelial tissue useful in wound healing.

SUMMARY OF THE INVENTION

Novel methods have now been discovered for cryopreserving confluent sheets of living, cultured epithelial cells so that they maintain their utility as a skin wound dressing. This methodology maintains the colony-forming efficiency of the cells in the sheet, i.e., preserves a significant number of living cells in the epithelial sheet in a mitotically competent form, such that regeneration of a healthy epithelium occurs. The methods also permit harvesting of cultured epithelial sheets when they are mature and warehousing the sheets in a cyropreserved form for future use.

The methods involve the following steps: 1) immersing the sheet in a cryoprotectant solution containing at least a non-cell-penetrating, glass-forming agent and, preferably, a cell-penetrating, glass-forming agent; 2) freezing the sheet by cooling it to a temperature at or below at least about −65° C., more preferably at or below −120° C. (the glass transition temperature of water), and most preferably, at or below −180° C. particularly for longer periods of storage. The preferred method involves cooling in the range of approximately −180° C. to approximately −196° C., preferably by exposure to the vapors of liquid nitrogen. The process further involves 3) storing the sheet at a temperature ranging from and below at least −65° C. and down to approximately −180° C.; and 4) thawing to produce an intact sheet wherein the cells have a colony-forming efficiency of at least 35%, often 40%, and in many cases 50% or more.

The cryoprotectant solution contains (on a weight percent basis) about 5% to 20% of a non-cell-penetrating, glass-forming agent, preferably about 15%, and about 10% of a cell-penetrating glass-forming agent. The cell-penetrating glass-forming agent may be glycerol, propylene glycol, ethylene glycol, dimethyl sufoxide (DMSO), and mixtures or derivatives thereof. Preferably, the cell-penetrating glass-forming agent is glycerol. The non-cell-penetrating glass-forming agent may be dextran, polyvinyl pyrrolidone, hydroxyethyl starch, chondroitin sulfate, polyethylene glycol, and mixtures or derivatives thereof, and is most preferably dextran or hydroxyethyl starch.

In preferred embodiments, the freezing step entails slowly cooling the sheet at least from about 4° C. to approximately −80° C., and further cooling to a temperature in the range of approximately −180° C. to approximately −196° C., i.e., the temperature of liquid nitrogen vapors. The slow cooling is conducted at a rate of about 1° C./minute. Additionally, the thawing step preferably entails heating the sheet, e.g., in air or other gas, from the low storage temperature up to the range of −120° C. to about −80° C. in a time between about 1 minute and 5 minutes, i.e., at a heating rate of about 20° C./min. to about 100° C./min. The sheet then may be incubated in an aqueous bath or otherwise rapidly heated to increase the temperature further up to about 20° C. to about 37° C.

Prior to use as a skin wound dressing, the thawed sheet is rinsed free of cryoprotectant using, for example, an isotonic buffer solution at physiological pH, preferably lactated Ringer's solution, in which cells can be stored temporarily before use. The epithelial cells of sheets used in the method preferably are cultured keratinocytes. The confluent sheet is several cells thick, and comprises differentiating layers.

Other objects and features of the invention will be apparent from the drawing, description, and claims which follow.

DETAILED DESCRIPTION

Figure 1:
FIG. 1 is a cross section of a stratified cultured keratinocyte sheet after being released from a culture flask with Dispase. The photomicrograph is representative of a stratified cultured keratinocyte sheet used in the practice of this invention.

Cultured human epithelial cell sheets can function as permanent autograft material for repair of skin wounds. As temporary allograft material, the sheets can promote healing of chronic skin ulcers and split-thickness graft donor sites and may also provide a highly effective burn wound dressing. The sheets are produced using a culture system developed by Rheinwald and Green, wherein serially cultured epithelial cells divide rapidly on the surface of tissue culture dishes or flasks and ultimately form a confluent, modestly stratified polarized sheet of tightly interconnected cells. A photomicrograph of a cross section of such a cultured sheet is shown in FIG. 1. Stratified epithelial cultures can be released as cohesive cell sheets by treatment with an enzyme such as dispase, stapled to gauze impregnated with an nonadherent material, e.g., petrolatum or Vaseline ®, transported in culture medium to the operating room, and applied to the patient.

A significant limitation in the use of cultured epidermal grafts is their extreme fragility and short shelf life. Experiments indicated that cell viability in the grafts decreased substantially when the grafts had been separated from their culture substratum for longer than 8 hours, as measured by the ability of disaggregated cells to resume growth and form colonies when replated under optimal culture conditions. For this reason, sales of cultured epithelial sheets have been limited geographically, i.e., to those hospitals near enough to a production center so that the grafts could be prepared, transported, and applied to the patient within about 8 hours or less from the time dispase was first added to the cultures to initiate detachment at the culture facility. Actual time in transit could only be a few hours as time was consumed in preparing the grafts. Operating room scheduling and time of arrival of the grafts had to be coordinated carefully. Storage of the sheets for any significant period has been impossible, and therefore an inventory of ready-to-use product could not be maintained.

A possible explanation for such a short period of viability of detached epithelial cell sheets was provided by the observation that epithelial cells are found to lose the potential for further division and commit to terminal differentiation when, as single cells disaggregated from cultures by trypsin and EDTA treatment, they are temporarily maintained under conditions that prevent them from reattaching to a surface.

Experiments assessing viability beyond eight hours revealed that the temperature at which the dispase-treated grafts were maintained was extremely critical to cell viability as measured by colony forming efficiency (CFE) and the total number of colony-forming cells recovered (CFC, or total cells recovered X CFE). Maintenance of the cultured epithelial sheets at or slightly below physiological temperature failed to maintain the CFE of fresh tissue. Similarly, maintenance at 4° C. had no apparent positive effects, despite careful control of media conditions, pH, and $CO_2/O_2$ balance. CFE can be maintained for greater than about 20-30 hours if the cultured sheets are maintained within a critical temperature range of 10° C. to 25° C., preferably 13° C. to 23° C. However, no method is currently available for storing the cultured sheets for more than one day while maintaining their utility as a skin wound dressing, and maintenance of an inventory of a ready-to-use product for wound healing applications has not been possible The history of cryopreservation methodology has shown that the optimization of a cryopreservation protocol for a particular cell does not necessarily give good results when used with another cell type or when used with the same cell type from a different species, or with other cells in a tissue. Methods for freezing a suspension of keratinocytes yield poor results when used for intact sheets. In fact, freezing intact tissues for use in implants has not, to our knowledge, been successful for any tissue type (but see Cancedda et al., EP 0 296 475).

The methods disclosed herein of cryopreserving a confluent sheet of living, cultured epithelial cells after separation from their culture substratum maintain the mitotic competence, or colony-forming efficiency of the cells in the sheet at acceptable levels, and maintain the integrity of the sheet. Briefly, the method comprises four steps. First, the cell sheet is equilibrated in a cryopreservative solution for a time sufficient to allow the cryopreservative to mix thoroughly with and/or displace the water within and between the cells. Second, the sheet is cooled preferably to approximately −180° C. to −196° C., at a rate slow enough for the cryoprotected cells to avoid ice crystal formation and subsequent damage. The frozen sheets may be stored for long periods at approximately 31 180° C. or for shorter periods at higher temperatures, e.g., as high as about −65C. Before use, the sheets are warmed at room temperature in air or other gas for about 1-3 minutes, and then thawed completely by rapid warming in, for example, a water bath. Fourth, the cryoprotectant is removed from the cultured epithelial cell sheet by rinsing in an isotonic buffer such as lactated Ringer's solution.

Details of the procedure are disclosed below.

Preparation of Cultured Epithelial Sheets

Epidermal cells (keratinocytes) are seeded into T150 culture flasks (Costar) at densities that will reach confluence in 10-12 days. Cultures from frozen cell suspensions from several epidermal cell strains may be used for allografts; cells from biopsies of burn patients for autografts. Cultures are maintained in gas tight flasks at 37° C. in "FAD" medium (one part Hams F12 supplemented with adenine and 3 parts Dulbecco's modified Eagle's medium (DME) plus 10% fetal bovine serum (FBS), 0.4 μg/ml hydrocortisone, $1 \times 10^{-10}$M cholera toxin, and $2 \times 10^{-9}$M triiodothyronine) and grown in the presence of lethally irradiated 3T3 fibroblasts. See U.S. Pat. No. 4,016,036. Ten ng/ml epidermal growth factor is included from the first feeding.

The cell cultures are used to prepare grafts once they have reached confluence. The supernatant medium is aspirated and 40 ml of Dispase II (Boehringer Mannheim) at a final concentration of 2.5 mg/ml (approximately 1.2 U/ml) is added to the flasks and incubated at 37° C. When the edges of the sheet become detached (~45 min.), the upper portion of each flask is removed by burning with a soldering iron.

The enzyme solution is replaced by 20 ml of DME medium. The sheet of epithelial cells then is rinsed again with 20 ml of DME. After aspirating all but 3-4 ml of the second rinse, 5×10 cm pieces of Petroleum jelly (Vaseline ®)-impregnated gauze (Cheesebrough Ponds) are placed over each detached sheet of cells with the superficial cells facing the gauze dressing. The cohesive cell sheet is then attached to the dressings with 12-15 staples (Ligaclips, Ethicon/J&J). The sheet is cut widthwise, stapled, and the grafts are then transferred to 100 mm dishes with the epithelium facing up. The edges of the graft are pressed to the dish with a rubber policeman to prevent the graft from floating. Twelve ml of DME is gently added and the dish is transferred to the storage container. (FIG. 1 illustrates in cross-section a typical cultured sheet made in accordance with the foregoing process). Cell recovery (R) and assay of colony forming efficiency (CFE) are used to determine the total number of mitotically competent cells (CFC). In this manner, the optimal conditions for preserving viability during the cryoprotective process can be determined, e.g. composition of cryoprotective medium, equilibration time in cryoprotective medium prior to freezing and after thawing, freezing rate, storage temperature, thawing process, rinsing procedure, and subsequent storage.

Colony-forming efficiency (CFE) assays are performed on the grafts prepared as set forth in the examples to follow, after storage for 1-3 days after freezing. Non-frozen graft are assayed as controls. Ligaclips are removed with forceps and the released cell sheet is dissociated to a single cell suspension in a mixture of trypsin (0.05%) and EDTA (0.01%) in isotonic buffer. Enzymatic action is arrested by addition of calf serum and is followed by two serial 1:10 dilutions made by adding 0.5 ml cell suspension to 4.5 ml FAD. An aliquot of the initial cell suspension is counted in a hemocytometer. A final concentration of 1,000-2,000 cells/ml is prepared and 1 ml of cell suspension is plated into 100 mm dishes containing lethally irradiated 3T3 cells in 12 ml of FAD medium.

After 10-14 days, cultures are fixed with 10% formalin in phosphate buffered saline and stained with a mixture of 1% Rhodamine and 1% Nile Blue A. Colonies are counted under a dissecting microscope and scored as either growing or aborted. CFE is calculated as follows:

$$CFE = \frac{\text{total no. of colonies}}{\text{no of cell plated}}$$

Percent recovery, and percent CFE are calculated, respectively, as follows:

$$\frac{R_{FZ}}{R_{FS}} \times 100 = \% \text{ recovery; and}$$

-continued $$\frac{CFE_{FZ}}{CFE_{FS}} \times 100 = \% \ CFE.$$

where FZ is frozen, FS if fresh.

The total recovery of colony forming cells (CFC) is calculated as follows:

CFC = fraction of total cells recovered (R) × fraction of recovered colony forming efficiency (CFE), therefore $$CFC = \frac{CFE_{FZ} \times R_{FZ}}{CFE_{FS} \times R_{FS}} \times 100$$

Using protocols of the invention, % CFE's typically exceed 35%, usually exceed 40%, and often are greater than or equal to 50%.

Cryopreservation Protocol

Development of a cryoprotective methodology requires optimization of each individual component in the process through independent study followed by an integrated approach, combining optimal components, to identify the final process. Optimal freezing, storing, thawing, and rinsing procedures that are compatible with maintaining maximal viability must be identified. These components are identified by colony forming efficiency assay as described previously.

Figure 2:
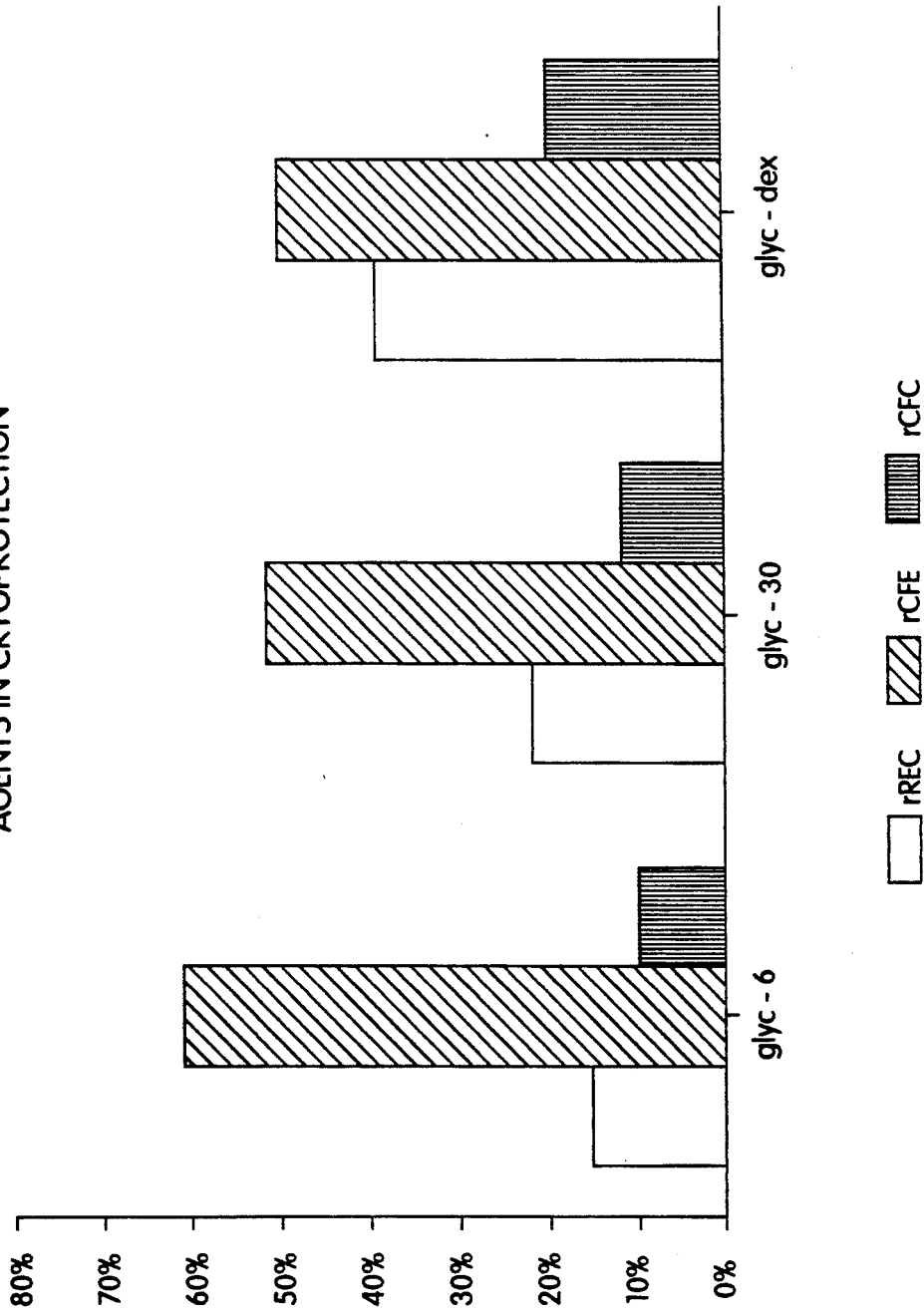
FIG. 2 is a bar graph illustrating the effects of the use of non-cell-penetrating agents in cryoprotection. Cultured keratinocyte sheets were equilibrated in cryoprotective medium (CPM) containing either 10% glycerol for 6 minutes (gly c-6) and 30 minutes (gly c-30), or 10% glycerol with 15% dextran (70 kd) for 30 minutes, then cooled to −180 C, and stored 2-3 days at −180 C. After thawing the viability was measured by assessing the total cell recovery (R), colony forming efficiency (CFE), and survival of colony forming cells (CFC) after disaggregation of the cell sheet. CFC=cells recovered X CFE of the recovered cells (expressed as a percentage of non-frozen, non-stored control sheets)

Standard cryoprotective medium is composed of a physiologically balanced salt solution (e.g., cell culture medium) supplemented with bovine serum and glycerol, a cell-penetrating glass-forming agent. Although used successfully for cryopreserving cells in suspension, its ability to preserve viability of cells from cell sheets is less clear. FIG. 2 demonstrates the beneficial effects of supplementing standard cryoprotective medium with an additional component, a non-cell-penetrating glass forming agent, such as dextran. Note the increased cell recovery and, therefore, greater viability (CFC) obtained when the non-cell penetrating agent is used in conjunction with the cell-penetrating agent, as compared with using the cell-penetrating agent alone.

Figure 3:
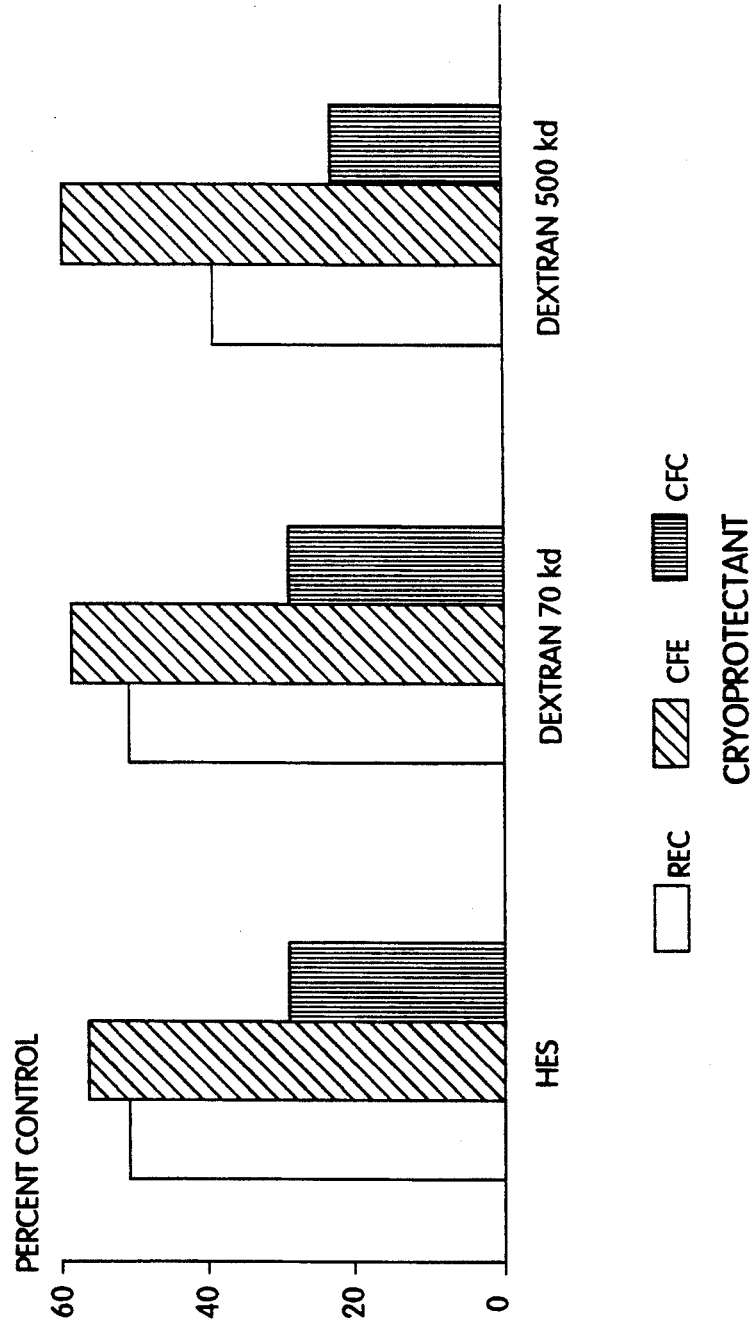
FIG. 3 is a bar graph illustrating the effect of dextran and Hespan (hydroxyethyl starch) on viability of cryopreserved cultured epidermal grafts. Grafts were equilibrated in CPM containing either 15% Hespan, 15% dextran (70 kd), or 15% dextran (500 kd), in addition to 10% glycerol, for 30 minutes, then cooled to −180° C. and stored for 2 days. After thawing viability was measured by assessing R, CFE, and CFC. Results are expressed as a percentage of non-frozen, non-stored control grafts.

FIG. 3 illustrates the general phenomenon of increasing viability through use of non-cell penetrating glass forming agents. These agents are high molecular weight forms of complex carbohydrates. The non-cell-penetrating glass-performing agent is preferably a high molecular weight dextran of approximately 50-500 kilodaltons (kd), preferably 50-70 kd, chondroitin sulphate, polyvinylpyrrolidone, polyethylene glycol or a hetastarch such as hyroxyethyl starch. The cell-penetrating glass-forming agent is preferably glycerol, but may include propylene glycol, ethylene glycol, dimethylsulfoxide, and other penetrating glass-formers known in the art.

Figure 4:
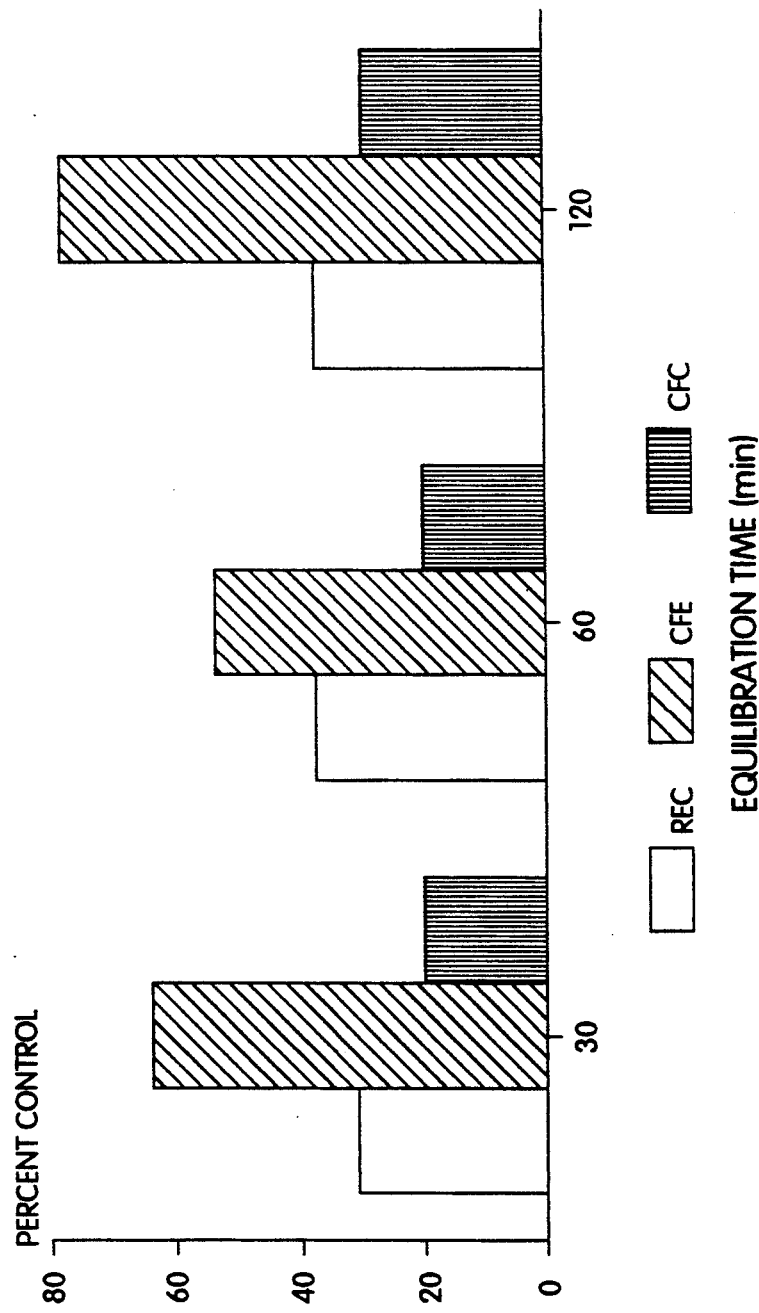
FIG. 4 is a bar graph illustrating the effect of cryoprotective medium prior to freezing on viability of cryopreserved cultured epidermal grafts. Grafts were equilibrated at room temperature in cryoprotective medium containing 15% dextran (70 kd) and 10% glycerol for 30, 60, and 120 minutes. After thawing, cells in grafts were assayed for R, CFE, and CFC. Results are expressed as a percentage of control grafts.

The cryopreservation process first requires immersion of the cell sheet to be frozen in cryoprotective medium for a time sufficient to permit equilibration of the cells with cryoprotectant. FIG. 4 demonstrates the effect of long-term equilibration of cultured epidermal sheets in cryoprotectant prior to freezing on viability. The data show that the sheet may be equilibrated for up to two hours in cryoprotectant prior to freezing without affecting the viability of cells within cryopreserved sheets. The equilibration is conducted more typically for approximately 30-60 minutes, at about 17° C. to 30°

C., typically room temperature, in a cryoprotective solution, in a shallow storage dish.

Following equilibration, the dish containing the sheet and the cryoprotectant solution is sealed so that it is gas and water-tight. The sheet in the sealed container is cooled to at least about −65° C. (e.g., with dry ice), preferably below −120° C., and to Promote longer term storage, to approximately −180° C. to about −196° C. The cooling rate preferably is slow (e.g., ≦1° C./min.) from about 0° C. to at least −80° C. This serves to discourage ice crystal formation. Preferably, cooling is conducted at the outset in a rate-controlled cooling device such as a commercial programmable cell freezer (Cryomed, Inc. No. 1010/2700) to a temperature of −40° C. to −100° C., Preferably about −80° C. to −85° C., and then transferred to a liquid nitrogen storage vessel and maintained in vapors of liquid nitrogen to reduce its temperature further.

The preferred freezing protocol cools the sheet in the sealed container until the tissue is approximately 4° C. Then, the sheet is cooled at about 1° C. Per minute. Once the temperature of the sheet reaches at least −65° C., and preferably at least −85° C., the container is transferred to a liquid nitrogen refrigerator and stored at approximately −180° C. (nitrogen vapors) or −196° C. (liquid nitrogen).

Figure 5:
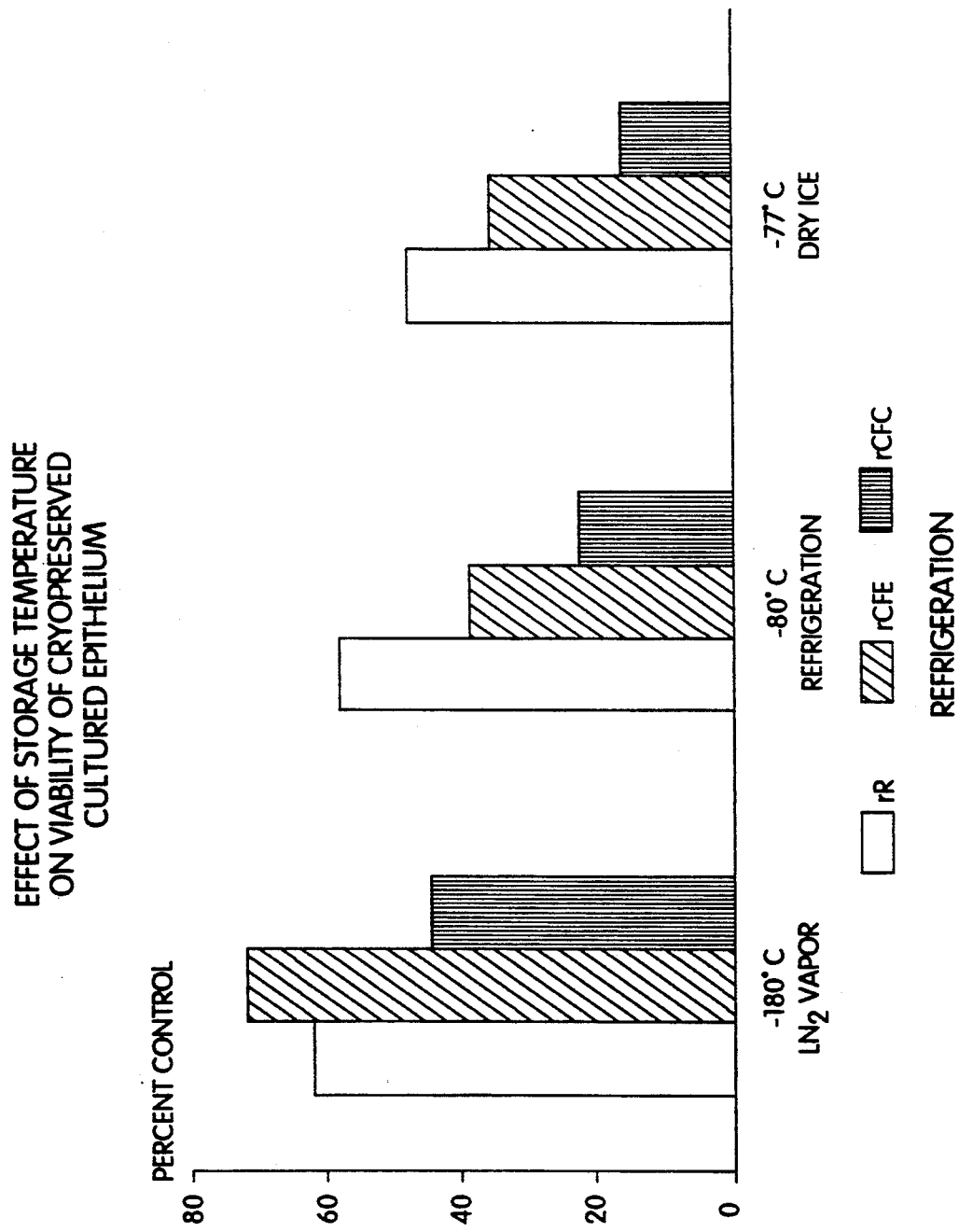
FIG. 5 is a bar graph illustrating the effect of storage temperature on viability of cryopreserved cultured epidermal grafts. Grafts were equilibrated at room temperature in CPM containing 15% dextran and 10% glycerol for 30 minutes, frozen to −85° C. and then stored at about −180° C. in liquid nitrogen vapor, at −80° C. in a mechanical freezer, or with solid carbon dioxide (dry ice, sublimation point −77° C.) at a temperature of about −65° C. After thawing, R, CFE, and CFC of the grafts were measured. Results are expressed as a percentage of control non-frozen, non-stored grafts.

Storing the tissue at or below −180° C. maintains the colony-forming efficiency of the cells better than storing the sheet at higher temperatures, as shown in FIG. 5. The data clearly indicate that storage at −180° C. in liquid nitrogen vapor is superior to storage at −80° C. in a mechanical freezer or at about −77° C. in dry ice. Since there is a dramatic decrease in viability during the first 2 or 3 days of storage at −80° C. and −77° C., in contrast to stable viability at −180° C. over longer periods. Grafts preferably are shipped at −180° C.

To thaw the sheet, the sealed container is removed from the liquid nitrogen refrigerator and preferably kept at room temperature in air for about 1 minute and up to about 3 to 5 minutes. This produces a warming rate of between about 20° C./min. to about 100° C./min. The graft may then be heated to room temperature without regard to the rate of heating. Preferably the last stage is conducted by submerging the sealed container in a water bath until the graft is thawed. This prevents the frozen sheet from cracking. Thawing is accomplished in about 1.25 minutes in a water bath at 37° C. If the water bath is 25° C., thawing takes about 1.5 minutes. Alternatively, the waterbath may be eliminated, and the sheet thawed at room temperature. However, this takes about 27 minutes and often has the effect of reducing cell viability.

The thawed sheet is removed from the cryoprotectant within about 1 hour, preferably as soon as possible. Once the sheet is thawed, the container may be opened and the cryopreservative solution replaced with an isotonic buffer solution at physiological pH (about 6.8–7.4), preferably FAD medium or lactated Ringer's solution to dilute out the cryoprotectant. Table 1A shows that not all isotonic buffered solutions at physiological pH are acceptable for dilution of cryoprotectant. Phosphate buffered saline and standard saline reduce viability significantly, as judged by CFE. The thawed sheet is equilibrated in rinsing buffer preferably for 15 minutes and may remain for up to 4 hours with a slight decrease in CFE (Table 1B).

TABLE 1A

Removal of cryoprotective medium from cryopreserved cultured epidermal grafts after thawing. Use of isotonic buffers at physiological pH as rinsing solutions.

| Buffer | % of cells forming colonies | rCFE |
|---|---|---|
| FAD | 9.0 | 35.0 |
| PBS | 3.4 | 13.1 |
| Normal saline | 3.0 | 11.5 |

Grafts were removed from cryoprotective medium and placed in rinsing solution for 15 minutes at room temperature. Colony forming efficiency assays were performed and the recovery of CFE (rCFE) was calculated as a percent of non-frozen, non-stored control grafts. FAD, F12/DME keratinocyte growth medium; PBS, Phosphate Buffered Saline; Normal saline, 0.9% saline.

TABLE 1B

Effect of increased rinsing time on thawed grafts

| Time | % of cells forming colonies | rCFE |
|---|---|---|
| 1 hour | 6.4 | 71.1 |
| 2 hours | 5.2 | 57.8 |
| 4 hours | 4.5 | 50.0 |

Grafts were removed from cryoprotective medium and placed in FAD rinsing solution for times indicated above at room temperature. Colony forming efficiency assays were performed and the recovery of CFE (rCFE) was calculated as a percent of non-frozen, non-stored control grafts.

Figure 6:
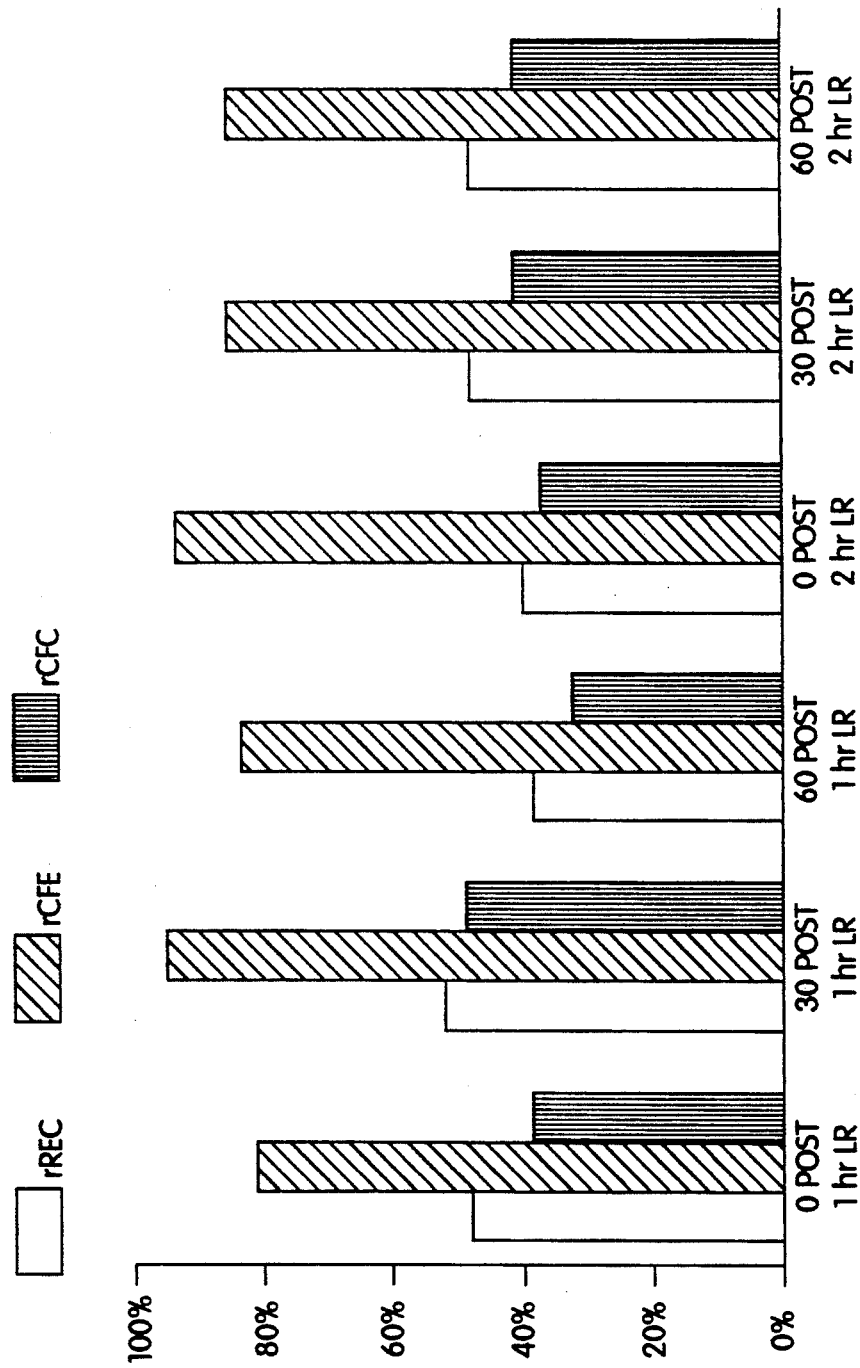
FIG. 6 is a bar graph illustrating the effect of post-thaw treatment of cryopreserved culture epidermal grafts. Grafts were equilibrated for 60 minutes in cryoprotective medium prior to freezing. After freezing and storage at −180° C. for 1-3 days, grafts were thawed rapidly, removed from CPM after 0, 30, or 60 minutes post thawing and rinsed for 1 or 2 hours in lactated Ringer's solution. Cell recovery, CFE, and CFC of the treated grafts were measured and expressed as a percentage of control non-frozen, non-stored grafts.

Some of the limits of the final process of cryopreservation were tested and are shown in FIG. 6. The data show that cultured epithelial sheets can be equilibrated in cryoprotectant prior to freezing for up to one hour, frozen, thawed, left in cryoprotectant up to one hour post-thaw and finally rinsed in lactated Ringer's solution for up to 2 hours, producing an intact sheet of cells which are viable and capable of resuming normal metabolic function.

A sheet prepared as disclosed above may be placed surgically over a clean skin wound such as a burn or ulcer, using the gauze backing as a dressing, with the germinative layer in contact with the surface of the wound. Allograft sheets eventually are sloughed off, but prior to rejection provide safe and effective protection to the wound, and often promote wound healing. Autograft sheets typically take permanently and differentiate to produce intact, normally stratified skin. The higher CFC and CFE values that are achieved with this cryopreservation methodology demonstrates that greater numbers of individual cells in the sheet are mitotically competent, and therefore implies that a greater number of epithelial cell colonies will form at the wound site.

The invention will be illustrated further by means of the following, non-limiting Examples.

EXAMPLE I

The harvested cultured graft is placed in a shallow storage dish in a cryoprotectant solution comprising 15% dextran (70,000 mw) and 10% glycerol in medium. The container is sealed so that it is gas and water-tight, and contains enough liquid such that little or no air space remains and the grafts are equilibrated at room temperature for 30 min.

The sheet is cooled in the sealed container until the tissue is approximately 4° C. The sheet is then cooled at 1° C. per minute to approximately −85° C. Once the temperature of the sheet reaches −85° C., the container is transferred into a liquid nitrogen refrigerator and thereafter stored in liquid nitrogen vapor (about −180° C.).

To thaw the sheet, the sealed container is removed from the liquid nitrogen freezer and kept at room temperature in air for approximately 1 minute. It is then placed in a 37° C. water bath for approximately 75 sec., until thawed. Once thawed, the container is opened and the sheet is placed in lactated Ringer's solution at physiological pH for 5 min. The buffer then is changed, and the sheet is equilibrated in the medium for at least another 10 min.

EXAMPLE II

The graft is equilibrated in a shallow storage dish in a cryoprotectant solution comprising 15% hydroxyethyl starch (Hespan ®) and 10% glycerol at room temperature for 15 min. Following equilibration, the container is sealed so that it is gas and water-tight.

The sheet in the sealed container is cooled until the tissue is approximately 4° C. Following this step, the sheet is cooled at 1° C. per minute to approximately −85° C. Once the temperature of the sheet reaches −85° C., it is transferred into a liquid nitrogen refrigerator and stored in liquid nitrogen (approximately −196° C.).

To thaw the sheet, the sealed container is removed from the liquid nitrogen freezer and is kept at room temperature in air for approximately 1 minute. It is then placed into a water bath until thawed. Once thawed, the container is opened and the sheet is placed in lactated Ringer's solution or serum free DME/F12 keratinocyte growth medium at physiological pH for 5 min. After 5 min., the buffer is changed and the sheet equilibrated in the medium for up to 4 hours.

The invention may be embodied in other specific forms. Other embodiments are within the following claims.

What is claimed is:

1. An improved method for maintaining a cohesive sheet of living epithelial cells in a cryopreserved state, comprising the steps of:
   A. providing a cultured, stratified sheet of epithelial cells separated from its substratum;
   B. immersing said cultured sheet for greater than 15 minutes in a cryoprotective solution comprising a non-cell-penetrating, glass-forming agent which is removable by dilution and rinsing upon thawing, in combination with a cell-penetrating, glass-forming agent;
   C. cooling said sheet in the cryoprotective solution to a temperature of or below approximately −65° C.;
   D. storing the cooled sheet at a temperature at or below −65° C.; and
   E. thawing the cryopreserved sheet to produce an intact, mitotically competent sheet of viable cells capable of stratified differentiation, wherein said intact sheet is useful as a skin wound dressing.

2. The method of claim 1, wherein the cryoprotective solution comprises from about 5% to about 20% by weight of said non-cell-penetrating, glass-forming agent.

3. The method of claim 1, wherein the non-cell-penetrating, glass-forming agent is selected from the group consisting of dextran larger than 70 kilodaltons, polyethylene glycol, polyvinylpyrrolidone, hydroxyethyl starch, chondroitin sulfate and mixtures thereof.

4. The method of claim 1, wherein the non-cell-penetrating, glass-forming agent is dextran larger than 70 kilodaltons or hydroxyethyl starch.

5. The method of claim 4, wherein the agent is dextran having a molecular weight from approximately 70 kilodaltons to approximately 500 kilodaltons.

6. The method of claim 5, wherein said dextran is combined with the cell-penetrating agent, glycerol.

7. The method of claim 1, wherein the cryoprotective solution comprises about 10% by weight of a cell-penetrating, glass-forming agent selected from the group consisting of glycerol, dimethylsulfoxide and mixtures thereof.

8. The method of claim 6, wherein the cell-penetrating, glass-forming agent is glycerol.

9. The method of claim 1, wherein the immersion step is performed for a time sufficient to equilibrate the sheet with the cryoprotective solution.

10. The method of claim 9, wherein the immersion step is conducted for a time period of between 15 minutes and 180 minutes.

11. The method of claim 9, wherein the sheet is immersed for as long as 120 minutes in said cryoprotective solution at 17°–30° C. and then cooled to 4° C.

12. The method of claim 1, wherein the cooling step is conducted at a rate of about 1° C. per minute to cool the sheet from about 4° C. to below about −80° C.

13. The method of claim 1, wherein the sheet is cooled slowly to approximately −80° C. and then cooled to a temperature at or below −180° C.

14. The method of claim 1, wherein the cooling and storing steps are done to a temperature at or below −120° C.

15. The method of claim 1, wherein the cooling and storing steps are conducted in a rigid, transparent, sterile, gas impervious container.

16. The method of claim 1, wherein the storing step is performed at a temperature at or below approximately −180° C., whereby the storage interval may be increased.

17. The method of claim 1, wherein the sheet is cooled to a temperature below about −180° C. and the thawing of the sheet is accomplished by first incubating the sheet in air until the sheet reaches a temperature of between about −120° C. and −80° C. and then immersing the sheet in liquid until the sheet is thawed.

18. The method of claim 1, wherein the thawing step comprises allowing the sheet to warm up to about −80° C. over a period of time between about 1 minute and 5 minutes and then warming the sheet to room temperature.

19. The method of claim 1 comprising the additional step of:
   F. removing the cryoprotective from the thawed sheet by transferring said sheet to a rinsing solution selected from the group consisting of FAD medium and lactated Ringer's solution for a period of up to approximately four hours.

20. The method of claim 1, wherein step C is conducted by exposing the sheet to liquid nitrogen vapors.

21. The method of claim 1, wherein the epithelial cells are keratinocytes.

22. The method of claim 1, wherein the intact sheet of viable cells is characterized by a colony forming efficiency of at least 35%.

23. The method of claim 1, wherein prior to step B, the cultured sheet of epithelial cells is mounted on a supportive backing.

24. A method of warming a cryoprotectant impregnated, cultured sheet of epithelial cells from a temperature below about −180° C. to prepare it for application to a patient as a skin wound dressing, the method comprising of step of:
raising the temperature of the sheet to between about −120° C. and −80° C. at a rate of about 20° C. to about 100° C. per minute and thereafter increasing the temperature to between 20° C. and 37° C.

25. The method of claim 24, wherein the sheet is heated to the temperature of about −80° C. by exposure to a gas and then heated to between about 20° C. and 37° C. in a liquid.

26. The method of claim 24, comprising the additional step of removing the cryoprotectant impregnating said sheet by incubating said sheet in a rinsing solution selected from the group consisting of FAD medium and lactated Ringer's solution.

27. The method of claim 1, wherein the temperature for immersing said cultured sheet in step B is below about 30° C.

28. The method of claim 27, wherein said temperature is between about 17° C. and 30° C.

* * * * *